United States Patent
Page et al.

(10) Patent No.: US 11,193,920 B2
(45) Date of Patent: Dec. 7, 2021

(54) METHOD FOR THE AUTOMATED IN-LINE DETECTION OF DEVIATIONS OF AN ACTUAL STATE OF A FLUID FROM A REFERENCE STATE OF THE FLUID ON THE BASIS OF STATISTICAL METHODS, IN PARTICULAR FOR MONITORING A DRINKING WATER SUPPLY

(71) Applicant: Endress+Hauser Flowtec AG, Reinach (CH)

(72) Inventors: Rebecca Page, Basel (CH); Peter Huggenberger, Dornach (CH); Stefan Wiesmeier, Munich (DE); Daniel Waldmann, Aesch (CH)

(73) Assignee: Endress+Hauser Flowtec AG, Reinach (CH)

( * ) Notice: Subject to any disclaimer, the term of this patent is extended or adjusted under 35 U.S.C. 154(b) by 352 days.

(21) Appl. No.: 16/345,850

(22) PCT Filed: Oct. 17, 2017

(86) PCT No.: PCT/EP2017/076461
§ 371 (c)(1),
(2) Date: Apr. 29, 2019

(87) PCT Pub. No.: WO2018/077666
PCT Pub. Date: May 3, 2018

(65) Prior Publication Data
US 2019/0257806 A1 Aug. 22, 2019

(30) Foreign Application Priority Data
Oct. 28, 2016 (DE) .................... 10 2016 120 663.6

(51) Int. Cl.
| | |
|---|---|
| *G01N 33/18* | (2006.01) |
| *G06N 3/08* | (2006.01) |
| *G05B 13/02* | (2006.01) |
| *G16H 20/10* | (2018.01) |

(52) U.S. Cl.
CPC ........... *G01N 33/18* (2013.01); *G05B 13/027* (2013.01); *G06N 3/088* (2013.01); *G16H 20/10* (2018.01)

(58) Field of Classification Search
CPC ...... G01N 33/18; G05B 13/027; G06N 3/088; G16H 20/10
See application file for complete search history.

(56) References Cited

U.S. PATENT DOCUMENTS

| | | | |
|---|---|---|---|
| 2003/0236649 A1 | 12/2003 | Kodukula et al. | |
| 2009/0292195 A1 | 11/2009 | Boyden et al. | |

(Continued)

FOREIGN PATENT DOCUMENTS

| | | |
|---|---|---|
| CN | 105868853 A | 8/2016 |
| WO | 2016014610 A1 | 1/2016 |
| WO | 2016070195 A1 | 5/2016 |

OTHER PUBLICATIONS

William Ocampo-Duque, Carolina Osorio, Christian Piamba, Marta Schuhmacher, José L. Domingo, Water quality analysis in rivers with non-parametric probability distributions and fuzzy inference systems: Application to the Cauca River, Colombia, Environment International, vol. 52, pp. 17-28 (Year: 2013).*

(Continued)

*Primary Examiner* — Michael J Dalbo
(74) *Attorney, Agent, or Firm* — Christopher R. Powers; Endress+Hauser (USA) Holding Inc.

(57) ABSTRACT

A method for automated in-line detection of deviations of an actual state of a fluid from a reference state is disclosed wherein measured values captured at the same time are evaluated in a combined manner with respect to at least three measurement variables that are different measurement quantities of the fluid and/or a measurement quantity of the fluid measured at different measuring points. The method includes creating a reference data set, wherein reference (Continued)

measured values are mapped to a reference vector of a vector space using a neural network; in-line measurement, wherein measured values at all times are mapped to a measurement vector using the neural network; comparing the measurement vector with the reference vectors using a kernel density estimator of a predefinable window width; and creating an assessment with respect to a deviation of the actual state from the reference state on the basis of the kernel density estimator.

15 Claims, 2 Drawing Sheets

(56) References Cited

U.S. PATENT DOCUMENTS

| | | |
|---|---|---|
| 2016/0054162 A1 | 2/2016 | Hollaender et al. |
| 2016/0161310 A1 | 6/2016 | Leaders et al. |
| 2017/0076446 A1* | 3/2017 | Pedersen ............ A61B 5/445 |

OTHER PUBLICATIONS

Wang, Y., Wu, F., Giesy, J.P. et al. Non-parametric kernel density estimation of species sensitivity distributions in developing water quality criteria of metals. Environ Sci Pollut Res 22, 13980-13989 (Year: 2015).*
Page, Rebecca M., et al., "Multivariate Analysis of Ground water-Quality Time-Series Using Maps and Sammon's Mapping", Water Resour Manage, vol. 29, No. 11 (Jun. 13, 2015), pp. 3957-3970.
Search Report for German Patent Application No. 10 2016 120 663.6, German Patent Office, dated May 19, 2017, 7 pp.
Search Report for International Patent Application No. PCT/EP2017/076461, WIPO, dated Dec. 1, 2017, 11 pp.
Page, Rebecca M., Huggenberger, Peter and Lischeid, Gunnar, Multivariate Analysis of Groundwater-Quality Time-Series Using Self-organizing Maps and Sammon's Mapping, Water Resour Manage (2015) 29:3957-3970, Jun. 13, 2015, 14 pp.
Nikoo, Mahammad Reza, Mahjouri, Najmeh, Water Quality Zoning Using Probabilistic Support Vector Machines and Self-Organizing Maps, Water Resour Manage (2013) 27:2577-2594, Feb. 24, 2013, 18 pp.

* cited by examiner

METHOD FOR THE AUTOMATED IN-LINE DETECTION OF DEVIATIONS OF AN ACTUAL STATE OF A FLUID FROM A REFERENCE STATE OF THE FLUID ON THE BASIS OF STATISTICAL METHODS, IN PARTICULAR FOR MONITORING A DRINKING WATER SUPPLY

CROSS-REFERENCE TO RELATED APPLICATIONS

The present application is related to and claims the priority benefit of German Patent Application No. 10 2016 120 663.6, filed on Oct. 28, 2016 and International Patent Application No. PCT/EP2017/076461 filed on Oct. 17, 2017, the entire contents of which are incorporated herein by reference.

TECHNICAL FIELD

The invention relates to a method for the automated in-line detection of deviations of an actual state of a fluid from a reference state of the fluid. The invention further relates to a device designed to carry out the method.

BACKGROUND

In many applications of process and/or automation technology, the state of a fluid is determined and/or monitored, in particular with respect to the quality of the fluid, by means of measuring devices, in particular in-line measuring devices. A measuring device called an in-line measuring device detects a measurement quantity directly and immediately in the fluid to be monitored, without, for example, removal or pretreatment of a sample of the fluid being required. The Endress+Hauser Group produces and distributes a variety of such measuring devices.

In the case of measuring devices that do not have in-line capability, however, sampling by an application engineer is often necessary, possibly followed by a pretreatment of the sample to be analyzed, for example by adding reagents which result in a change in the sample that can be detected by optical or electrochemical sensors. In comparison to the aforementioned in-line measurement methods, significantly lower detection/determination limits can be achieved in this case with a higher degree of accuracy as well as selectively, that is, even in the presence of interfering substances. However, the lengthy measuring time required by sampling and pretreatment and thus the accompanying low measuring frequency are disadvantageous.

The following problem arises: In order to be able to detect changes in the fluid immediately, in particular in the quality state, i.e., with respect to the quality of the fluid, the use of in-line measuring devices is a necessary condition. On the other hand, an assessment based on the measured values captured with the in-line measuring devices, for example with respect to an increased hazard due to a contamination source, for example a disaster, is often difficult. In particular, unambiguously determining a potential hazard to the fluid quality on the basis of a single in-line measured value (such as, for example, electrical conductivity, temperature or pH value) is a great challenge.

In order to meet this challenge, a plurality of in-line measured values with respect to different measurement variables are often captured essentially simultaneously with a plurality of measuring devices. The measurement variables are, for example, different measurement quantities of the fluid and/or a measurement quantity of the fluid measured at different measuring points. The aim in this case is that on the basis of the totality of the measured values captured in-line with respect to different measurement variables, a statement be made about the state of the fluid with respect to the quality of the fluid, in particular also with respect to the change in the state of the fluid over time. Especially in complex systems, rapid evaluation of the actual state is required despite a large quantity of information, such as the measured values with respect to different measuring points and measurement quantities.

The task of making a combined evaluation of the measured values with respect to the measurement variables thus arises. For example, a multivariate data analysis of the measured values captured in-line is to be carried out in such a way that undesirable quality states of the fluid and a change in the fluid are detected immediately and reliably. This is especially true of fields of application in which a high level of reliability is required. In the context of the application, a relevant example is the assessment of untreated water and/or drinking water since a decrease in drinking water quality, for example as a result of a contamination with pathogenic germs, should be detected both immediately and reliably in order to rule out any risks for the population.

Different methods are known in the prior art for the multivariate data analysis of measured values, in particular also measured values (including so-called time series) acquired recurrently. One example is neural networks. Methods of multivariate data analysis based on neural networks are mostly self-learning methods.

An overview of a method based on neural networks, in particular with respect to the assessment of untreated water and/or drinking water, is described in the inaugural dissertation of R. Page, which was submitted at the University of Basel in 2011 under the title "Approaches to hazard-oriented groundwater management based on multivariate analysis of groundwater quality." In this work, a possibility was presented of performing a multivariate data analysis with respect to the monitoring of drinking water and/or untreated water by means of neural networks. The result is likewise published in the scientific article by R. Page et al. "Multivariate analysis of groundwater-quality time-series using self-organizing maps and Sammon's mapping" in the journal Water Resources Management, 29th edition, page 3957 et seq. in 2015. The method described therein combines a special form of neural networks, so-called self-organizing maps (SOM for short and also called Kohonen maps) with a Sammon error function. In this case, a dimensional reduction leads to a reduction in the complexity of the task of early detection of a hazard based on in-line measured values, wherein the necessary information content of the measured values is retained.

Substantially simultaneously recurrently captured measured values for each time ti are in this case mapped to a vector xti, wherein the Sammon error function E is minimized:

$$E = \frac{1}{\sum_{i<k} d_{ik}^*} \sum_{i<k} \frac{[d_{ik}^* - d_{ik}]^2}{d_{ik}^*}$$

Here, i and k denote two arbitrary times, where i=1, . . . , n and k=1, . . . , n is the number of times. $d^*_{ik}$ is the distance in the original vector space between the vector xti of the measured values captured at the time ti and the vector xtk of the measured values captured at the time tk. $d_{jk}$ is the distance between the associated vectors in the dimensionally reduced vector space based on the SOM calculations. By means of the minimized Sammon error function, a set of dimensionally reduced vectors is obtained which reproduce as best as possible the original pattern of measured value distribution.

The combination of SOM and the Sammon error function is referred to as SOM-SM. The SOM-SM method makes it possible to represent the multivariate time series, while retaining its relative distribution, in the form of vectors which are arranged in a dimensionally reduced vector space and which reproduce as a pattern the relationship of the measured values relative to each other at all measuring times. Based on this representation, the object is to obtain a specific criterion for assessing the fluid.

SUMMARY

The object of the invention is therefore to propose a reliable and automatable method for the in-line monitoring of a fluid, in particular of a fluid located in a process, by means of a neural network, wherein the method can in particular quickly detect and evaluate changes with respect to quality. The invention is also based on the object of obtaining a device designed for the method.

As regards the method, this object is achieved by claim 1.

Claim 1 relates to a method for the automated in-line detection of deviations of an actual state of a fluid from a reference state of the fluid, wherein measured values which are captured essentially at the same time are evaluated in a combined manner with respect to at least three measurement variables, wherein the measurement variables are different measurement quantities of the fluid and/or a measurement quantity of the fluid which is measured at different measuring points, comprising at least the following method steps of:

a) Creating a reference data set by means of the following steps:
  Recurrent in-line detection at n different times tj, j=1, ..., n of reference measured values in each case detected essentially simultaneously with respect to the at least three measurement variables, wherein the fluid is in the reference state when the reference measured values are detected;
  Storing the reference measured values;
  Arranging the reference measured values by means of a neural network and projection into a vector space having a reduced dimension d, wherein the reduced dimension d is smaller than the number of measurement variables so that the reference measured values detected at the time tj are in each case mapped to a reference vector rtj of the vector space;
  Storing the n reference vectors;
b) In-line measurement comprising:
  In-line detection of essentially simultaneously detected measured values with respect to the at least three measurement variables of the fluid at a time ti;
  Storing the measured values;
c) Recurrently performing method step b), wherein the measured values at time ti and the measured values at all times (t1, ..., ti−1) preceding time ti are recurrently arranged by means of a neural network and projected into the vector space of reduced dimension d so that the measured values detected at time ti are mapped to a measurement vector xti of the vector space;

d) Storing the measurement vector xti;
e) Comparing the measurement vector xti with the n reference vectors rtj by means of a kernel density estimator $p_h(xti)$ of the predefinable window width h $$p_h(xti) = \frac{1}{nh^d} \sum_{j=1}^{n} f\left(\frac{|xti - rtj|}{h}\right)$$

wherein $$f\left(\frac{|xti - rtj|}{h}\right)$$

is a probability density function;
f) Creating an assessment for the time ti with respect to a deviation from the reference state on the basis of the value of the kernel density estimator $p_h(xti)$.

In method step a) of the invention, a reference data set is thus first created by means of the reference state. The reference state is in this case defined as a state considered to be a normal state, in which the fluid is in an acceptable state with respect to quality, i.e., all requirements for the quality of the fluid are met. The acceptable state may be validated, for example, using a safety-critical, non-in-line measured measurement quantity. In the reference state, there is, for example, neither a contamination of the fluid nor an unusual operating state. Within a time interval, in which the fluid is in the reference state, measured values with respect to the in-line measurement variables are then detected recurrently (i.e., at different times tj). In the process, at any time tj, at least three different measurement variables are detected essentially simultaneously. By means of the reference measured values detected in the reference state, the range of the fluctuations is thus precisely mapped, to which the measurement variables are naturally subjected and which are accepted in terms of quality.

In this case, the time interval and the measuring frequency for the recurrent detection of measured values are preferably selected such that sufficient reference measured values for the measurement variables are available. This generally depends on the dynamics of the system with respect to operating and operational states to which the fluid in the reference state is subjected, for example a desired value curve for a filling of a reservoir. If, for example, the dynamics are essentially periodic dynamics, at least measured values within the time interval of one period should be taken. In the case of drinking water and/or untreated water, a typical time scale of about one week is often sufficient. A measured value frequency of approximately 6 measured values per hour will thus give approximately 1000 measuring times tj for the reference measured values.

The detected reference measured values at the n times are represented using a neural network and subsequent projection into a reduced vector space. The reference measured values detected at n different times tj, j=1, ..., n are thereby mapped in each case to a reference vector rtj.

Subsequently, at a time ti, in-line measured values are captured, which are then related to the reference measured values after arrangement in the neural network and projection. For this purpose, the arrangement in the neural network and the projection into the vector space of reduced dimension d are used, wherein at each time ti, a neural network with the measured values at time ti and with the measured values at all times (t1, ..., ti−1) preceding time ti is formed.

The measured values detected at each time ti are here mapped to a measurement vector xti.

The reduced dimension d is smaller than the number of measurement variables, i.e., in the case of three measurement variables, for example, d=2 at most. Since the dimension d and the selection of the measurement variables for the measured values and the reference measured values are identical, the measured values and the reference measured values are projected into the same vector space.

According to the invention, the kernel density estimator is used in method step f) to assess the measurement vector xti with respect to the set of all n reference vectors rtj:

$$p_h(xti) = \frac{1}{nh^d} \sum_{j=1}^{n} f\left(\frac{|xti - rtj|}{h}\right)$$

The kernel density estimator is also referred to as the Parzen window estimator. Here, h is initially a predefinable window width, and $$f\left(\frac{|xti - rtj|}{h}\right)$$

is a probability density function, wherein formed as argument of the probability density function is the magnitude of the difference between the measurement vector and the reference vector, divided by the predefinable window width h. This is done for each of the n reference vectors. The mean value is subsequently formed, taking into account the predefinable window width and the reduced dimension d.

The kernel density estimator is a measure of how likely the occurrence of the measurement vector xti is in light of the totality of the reference vectors rtj, j=1, . . . , n. The probability density function which the person skilled in the art would use as basis as distribution for the reference measured values is used in this case; this also depends on the process in question or on the dynamics of the fluid.

The advantages of the invention are as follows:

- An automated and fast, i.e., essentially immediate, assessment can be made on the basis of detected in-line measured values.
- For assessing the state of the fluid, in particular with respect to quality, no specific threshold values with respect to the in-line measurement variables need to be selected. The natural heterogeneity of the fluid in the reference state regarded as normal is detected by means of the reference data set. The use of a reference state means that previously unseen states and fluctuations with respect to quality can be detected and assessed without further details.
- In contrast to other methods based on neural networks, the neural network with the reference measured values is only formed once according to the invention. With the measured values, a neural network is in each case newly formed at each time ti. The change over time in the state with respect to quality thus becomes visible and is correlated with the history.

In this case, a neural network is formed with the totality of all n reference measured values. For each time ti, another neural network with the recurrently detected measured values is newly formed and a measurement vector xti is created. In the normalization of the data set of the measured values before the SOM calculation, the calculated mean value of the data set of the measured values and the standard deviation of the reference data set are, for example, used in order to also take into account different initial situations (e.g., seasonality) and system-inherent fluctuations. In the evaluation of the state at time ti with respect to quality, the measurement vector at time ti is compared with the set of all reference vectors. In the method according to the invention, the information content is optimized since the second neural network can adapt to the data set of the measured values and as much as possible of the original dynamics of the system thus be transferred to the reduced vector space. The reference vectors and the measurement vectors are created directly after the in-line detection of the measurement variables at time ti. By the method according to the invention, an essentially permanent and adaptive in-line monitoring of the actual state of the fluid, and as a result ultimately also an assessment of a process with respect to the fluid quality, is therefore made possible.

In an advantageous embodiment, the formation of the neural network and the projection are effected on the basis of a self-organizing map or Kohonen map (SOM), wherein the Sammon error function (SM) is used in the projection. With regard to this embodiment, reference is again made to the aforementioned scientific article "Multivariate analysis of groundwater-quality time-series using self-organizing maps and Sammon's mapping," in which the execution of the SOM-SM method is described in detail.

In one embodiment, the reduced dimension d is greater than one, preferably two.

In a preferred embodiment, the probability density function is the probability density function of a normal distribution.

$$f\left(\frac{|xti - rtj|}{h}\right) = 2\pi^{-d/2} \cdot \exp\frac{-(xti-rtj)^2}{2h^2}$$

Naturally, depending on the fluid and/or dynamics of the fluid, other probability density functions known from the prior art are also possible, such as, for example, that of gamma distribution, that of Cauchy distribution or Lorentz distribution or that of Weibull distribution.

In one embodiment, the predefinable window width is estimated by means of the standard deviation of the distribution of the reference measured values and/or a distance of quantiles of the distribution of the reference measured values.

In the prior art, the term "quantiles" refers to different areas of the distributions, wherein equally large portions (=quantile) of the distribution lie within each area. A known example is the median, by means of which the values of the distribution are divided into two areas of the same size. Quartiles are also often used which divide distributions into four equally large parts. The interquartile range refers to the difference between the third and the first quartiles, i.e., Q (0.75)–Q (0.25). The interquartile range comprises the middle 50% of the distribution and in the prior art is used as measure of dispersion.

An example is estimating the predefinable window width h of the kernel density estimator using the interquartile range IQ4R and the standard deviation σ:

$$h = 1.06 \cdot in, \frac{IQ4R}{1.34}\right\} \cdot n^{-\frac{1}{5}}$$

Naturally, the predefinable window width h can also be determined only by the interquartile range IQ4R or another quantile distance or the standard deviation.

In one embodiment, the fluid is assessed at time ti with respect to the deviation of the actual state from the reference state by means of a division into at least two different categories of the first type (Ka1, Ka2, . . . ). This division depends on whether the kernel density estimator $p_h(xti)$ exceeds or falls below a first upper and/or lower predefinable threshold value. Preferably, an upper and a lower threshold value exist.

In a preferred embodiment of the invention, the difference between the measurement vector xti and a second measurement vector xtk is taken into account in the assessment of the actual state of the fluid for the time ti. The second measurement vector xtk belongs to a time tk preceding time ti, i.e., k=1, . . . , i−1. The time tk can thus be, for example, the time ti−1 immediately preceding the time ti.

In this embodiment, the history of the system is also taken into account in addition to the assessment based on the kernel density estimator. The assessment of the fluid at time ti therefore takes place on the one hand with respect to the probability of the occurrence of the measured values at time ti with respect to the reference measured values (kernel density estimator criterion) and on the other hand with respect to the development or history of the measured values so that abrupt changes can be detected, for example. In order to assess the difference, the distance d_ik between the measurement vectors xti and xtk, i.e., d_ik=|xti−xtk|, is, for example, used.

In a development of this embodiment, the fluid is assessed at time ti with respect to the deviation by means of a division into at least two different categories of the second type. The division into the at least two categories of the second type depends on whether the difference between the measurement vector xti and the second measurement vector xtk exceeds or falls below an upper and/or lower predefinable threshold value.

In a particularly advantageous development, a warning system with at least two warning levels is used to display the deviation of the actual state from the reference state and to display the difference between the measurement vector xti and the measurement vector xtk. In this case, the warning system is based on a combination of the categories of the first and second types. Such a warning system was also presented in 2015 in the technical publication by R. Page and P. Huggenberger in the journal Aqua & Gas, no. 12, page 28 et seq., but without however specifying the specific criteria according to the invention for calculating the assessment criteria.

In the simplest case, this is a linear combination with equally or differently weighted linear coefficients. However, another possibility is also non-linear combinations. For example, the influence of the kernel density estimator (category of the first type) or that of the difference with respect to the history (category of the second type) can be introduced into the warning system with an exponential function, depending on whether the warning system is to be designed as sensitive to deviations of the actual state from the reference state or to the history of the fluid.

In an embodiment, the warning system displays at time ti the contribution of each measurement variable to the warning level.

In another embodiment, the warning system displays at time ti the contribution of the categories of the first and second types to the warning level.

If appropriate, the contributions of the measurement variables and/or of the categories of the first and second types are displayed in this development only for the case in which there is an elevated warning level.

In one embodiment of the method according to the invention, method step a) is performed for at least two different reference states of the fluid. Before performing method steps c)-f), the following method step a2) is carried out:

a2) One of the at least two different reference states is selected.

After method step a2), method steps c)-f) are then carried out with respect to the reference state selected. This means that for the assessment by means of the kernel density estimator in step f), the measured values are compared only with the reference measured values of the respectively selected reference state.

In an embodiment, the fluid is untreated water and/or drinking water. The untreated water and/or drinking water can originate, for example, in a temporary drinking water reservoir, a water catchment, an aquifer or a spring. The untreated water and/or drinking water may be in a container, such as a tank, reservoir of a pipeline, an observation tube and/or a groundwater well. However, the measuring points defined at the outset may also be close to each other in different wells or observation tubes of different depths, wherein the measuring points are in communication with each other (for example, through watercourses and/or water pipes).

In an embodiment of this embodiment, the two different reference states are defined by whether the untreated water and/or drinking water is subject to a pumping operation or not. Pumping operation is, for example, present in the case of groundwater pumping.

In another embodiment, the at least two different reference states are defined by whether the untreated water and/or drinking water originates in different sources, seawater plants and/or aquifers.

In one embodiment of the method, the measurement quantities are selected from the group of the following measurement quantities: fill level, temperature, turbidity, oxygen content, electrical conductivity, pressure, redox potential, flow rate, pH value, and spectral absorption coefficient.

In principle, other measurement quantities known from the prior art, in particular analysis measurement quantities, which can be measured in-line, are naturally also suitable.

With respect to the device, the object is achieved by claim 17. Claim 17 includes a warning system for the automated in-line detection of deviations of an actual state of a fluid from a reference state of the fluid. The device comprises a measurement arrangement comprising at least three in-line measuring devices. The device moreover comprises a computer program product. The in-line measuring devices and the computer program product are designed to execute the method according to the invention.

In an embodiment, the computer program product is designed to carry out the storing and/or processing of the reference measured values and/or the measured values at least partially on at least one server and/or in a cloud.

In summary, changes in a fluid located in a process can be detected, assessed and displayed quickly and immediately by means of the invention. In the exemplary embodiments, the change relates to the hazard potential of a state with respect to quality, as deviations of an actual state of a fluid from a reference state of the fluid and changes in the state of the fluid with respect to quality are evaluated. It should finally be noted that the invention is not limited to the systematic monitoring of the quality of water. Other application examples include, for example, the assessment of fluids in processes of the chemical and/or pharmaceutical or of the food processing industries.

BRIEF DESCRIPTION OF THE DRAWING

The invention is explained in greater detail with reference to the following figures. These show.

DETAILED DESCRIPTION

Figure 1:
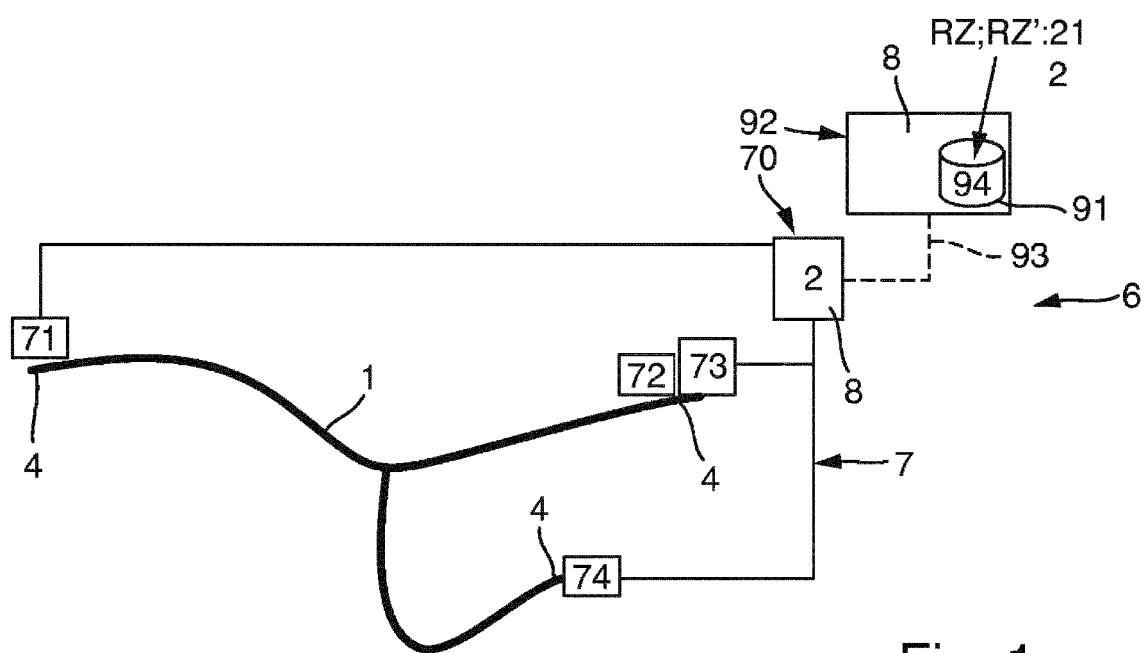
FIG. 1 shows an embodiment of the device according to the invention.

FIG. 1 shows a schematic diagram of an embodiment of a device according to the invention. The fluid 1 is shown here as a watercourse with three different measuring points 4. The measurement arrangement 7 comprises four different in-line measuring devices 71, 72, 73, 74 which detect the measurement variables MV1, MV2, MV3, MV4 essentially simultaneously. In this example, the measurement arrangement 7 also comprises a superordinate unit 70 to which the reference measured values 21 and the measured values 2 are transmitted. The fluid 1 is initially in a reference state RZ, wherein the reference measured values 21 are detected in a reference period (e.g., one week). The invention is of course not limited in any way to the exemplary embodiment shown here.

The reference measured values 21 are subsequently transmitted by a computer program product 8 via a data connection 93 to a database 94. The data connection 93 can take the form of, for example, an internet connection but also any other data connection known from the prior art. The database 94 can reside on a server 91, wherein the server in turn can at least partially be part of a cloud 92. The measured values 2 are also transmitted to the database 94 by means of the data connection 93. The computer program product 8 creates the assessment using the reference measured values 21, the measured values at time ti and the value of the kernel density estimator. This is carried out recurrently regularly for several times ti.

The device can in this case be part of a decentralized quality monitoring system, for example in a so-called 'software as a service' (SaaS for short) model, wherein only the warning levels W0, W1, W2 are transmitted and displayed. In this case, the warning level W0 indicates, for example, "no hazard," while the warning level W1 shows "slightly increased hazard" and the warning level W2 indicates "high hazard." On the basis of the warning levels W0, W1, W2, changes are thus transmitted essentially immediately, i.e., on-line, within the framework of a decentralized 24h monitoring system, wherein the monitoring takes place on the basis of in-line measuring devices 71, . . . , 74. In this case, for example, only in the event that the warning levels W1 or W2 are present, will the respective contributions made by the measurement variables MV1, MV2, MV3 to the warning level W1 or W2 be displayed. For example, if the warning level W1 is present and the contribution of the measurement variable MV1 to the warning level W1 is essentially 100% or just under 100%, the measuring device 72 assigned to the measurement variable MV1 at the respective measuring point 4 can, for example, be checked first. This provides both the aforementioned reliability but also prevents the occurrence of false alarms.

Figure 2:
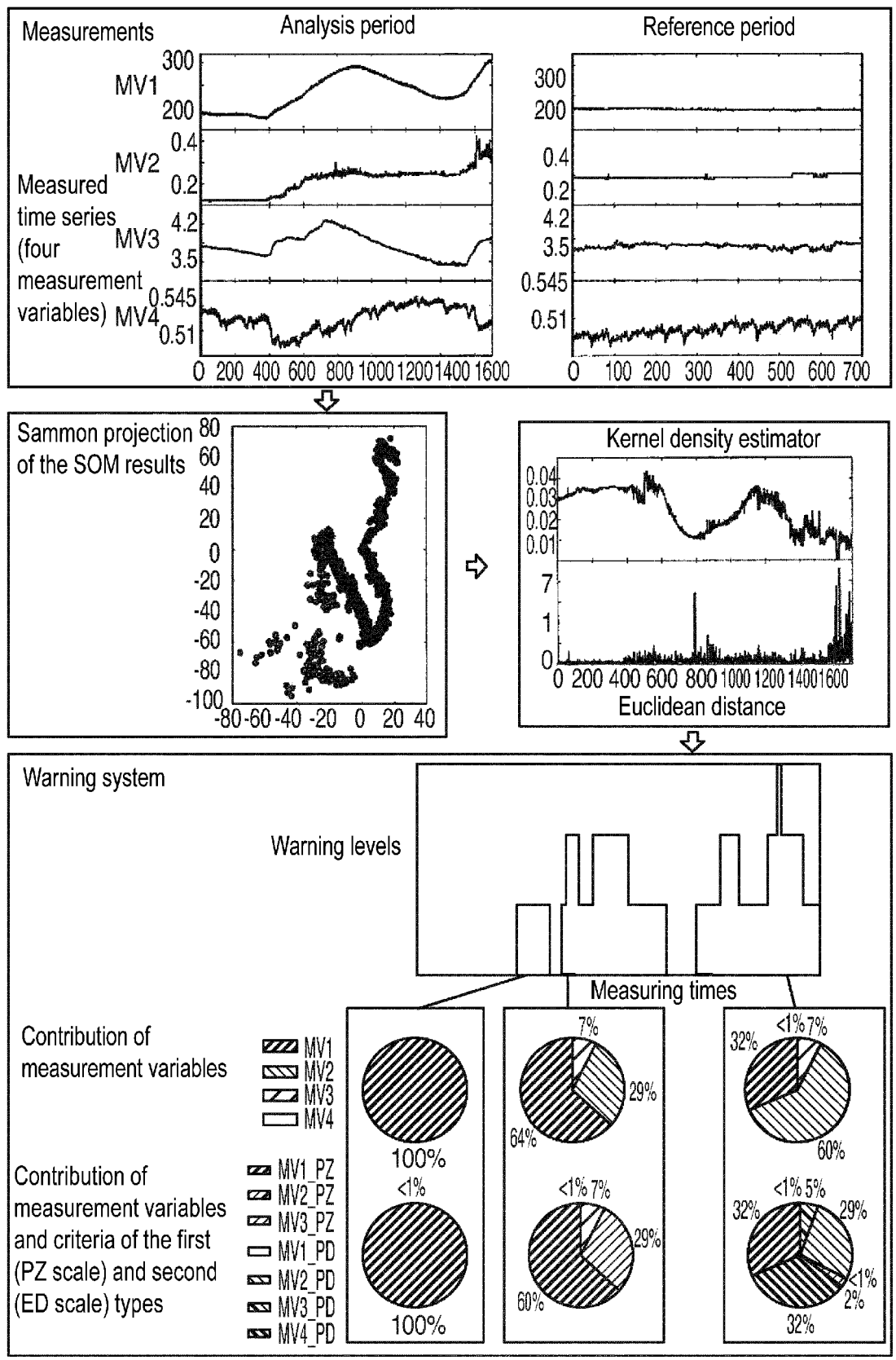
FIG. 2 shows an embodiment of the method according to the invention.

FIG. 2 shows a schematic of an embodiment of the method according to the invention. In this embodiment, the recurrent detection of the measured values 2 at times ti in the analysis period as well as the recurrent detection of the reference measured values 21 at times tj in the reference period are illustrated for the case of four measurement variables MV1, MV2, MV3, MV4. In the example, the reference period is approximately one week in which the fluid is present in a reference state RZ. In another embodiment, a plurality of such time series can also be present for the measurement variables MV1, MV2, MV3, MV4, in each case for a first reference state RZ and for a further reference state RZ'.

In an automated process, the neural network with the reference measured values 21 is created first, wherein the neural network is a SOM or Kohonen map. On the basis of the Sammon projection (SM) of the SOM results, the SOM-SM representation is obtained in which the n reference measured values 21 are projected onto n reference vectors rtj. A neural network, which is newly formed at each measuring time ti of the analysis period, is also created with the recurrently detected measured values 2. The measured values at the measuring times ti of the analysis period are in each case projected onto a measurement vector xti. The projected reference vectors rtj and the measurement vectors xti at each time tj and ti are vectors in a two-dimensional vector space VR.

The reference vectors rtj and the measurement vectors xti are compared directly after the in-line detection of the measurement variables at time ti. At each time ti, the value of the kernel density estimator is determined on the basis of the reference vectors rtj and the measurement vectors xti, wherein in this case the probability density function of a normal distribution is used as probability density function PDF:

$$p_h(xti) = \frac{1}{nh^d} \sum_{j=1}^{n} 2\pi^{-d/2} \cdot \exp{\frac{-(xti-rtj)^2}{2h^2}}$$

The predefinable window width h is in each case estimated as:

$$h = 1.06 \cdot in, \frac{IQ4R}{1.34} \cdot n^{-\frac{1}{5}}$$

At the same time, the Euclidean distance to the vector of the previous measuring time tk is calculated at each measuring time ti: |xti−xtk|. The measuring times tk and ti in this embodiment are directly consecutive measuring times (k=i−1). Other embodiments, wherein k=i−2, i−3, . . . , etc., are possible.

A warning level is then determined on the basis of a combination of the kernel density estimator $p_h$ (xti) and the Euclidean distance |xti−xtk|. In this exemplary embodiment, there are four warning levels W0 (no warning) as well as W1, W2, W3 (elevated warning levels). The contribution of the measurement variables MV1, MV2, MV3, MV4 to the warning level is then additionally displayed at the times ti at which a warning level is higher than W0, as well as the contribution of the kernel density estimator $p_h$(xti), also referred to herein as MV_PZ, and the Euclidean distance |xti−xtk|, also referred to herein as MV_ED.

The invention claimed is:

1. A method for the automated in-line detection of deviations of an actual state of a fluid from a reference state of the fluid, wherein measured values captured substantially at the same time are evaluated in a combined manner with respect to at least three measurement variables, wherein the measurement variables are different measurement quantities of the fluid and/or a measurement quantity of the fluid measured at different measuring locations, the method comprising:

a. creating a reference data set by:
  recurrently detecting reference measured values in-line at n different times, the reference measured values detected substantially simultaneously with respect to the at least three measurement variables, wherein the fluid is in the reference state when the reference measured values are detected;
  storing the reference measured values;
  arranging the reference measured values using a neural network and projection into a vector space having a reduced dimension, wherein the reduced dimension is smaller than the number of measurement variables such that the reference measured values detected at a given time are each mapped to a reference vector of the vector space; and
  storing the n reference vectors;
b. performing an in-line measurement including:
  in-line detection of substantially simultaneously detected measured values with respect to the at least three measurement variables of the fluid at a time ti; and
  storing the measured values;
c. recurrently performing step b, wherein the measured values at time ti and the measured values at all times preceding time ti are recurrently arranged using the neural network and projected into the vector space of reduced dimension such that the measured values detected at time ti are mapped to a first measurement vector of the vector space;
d. storing the first measurement vector;
e. comparing the first measurement vector with the n reference vectors using a kernel density estimator of a window width using:

$$p_h(xti) = \frac{1}{nh^d} \sum_{j=1}^{n} f\left(\frac{|xti - rtj|}{h}\right)$$

wherein $p_h(xti)$ is the kernel density estimator, h is the window width, d is the vector space dimension, n is the number of reference vectors, xti is the first measurement vector, rtj is the reference vectors, and $$f\left(\frac{|xti - rtj|}{h}\right)$$

is a probability density function; and
f. creating an assessment for the time ti with respect to a deviation of the actual state of the fluid from the reference state based on a value of the kernel density estimator.

2. The method of claim 1, wherein the neural network and the projection are formed using a self-organizing map or Kohonen map, wherein a Sammon error function is used in the projection, and/or wherein the reduced dimension of the vector space is two.

3. The method of claim 1, wherein the probability density function is the probability density function of a normal distribution:

$$f\left(\frac{|xti - rtj|}{h}\right) = 2\pi^{-d/2} \cdot \exp^{\frac{-(xti-rtj)^2}{2h^2}}$$

4. The method of claim 1, wherein the window width is estimated using a standard deviation of a distribution of the reference measured values and/or a distance of the quantiles of the reference measured values.

5. The method of claim 1, wherein the assessment of the fluid at the time ti with respect to the deviation of the actual state from the reference state is effected by a division into at least two different categories of the first type, and wherein the division depends on whether the kernel density estimator exceeds or falls below a first upper and/or lower threshold value.

6. The method of claim 1, wherein the difference between the first measurement vector and a second measurement vector is used in the assessment of the actual state of the fluid for the time ti, wherein the second measurement vector belongs to a time tk preceding the time ti.

7. The method of claim 6, wherein a division into at least two different categories of a second type is made during the assessment of the actual state of the fluid at the time ti, and wherein the division depends on whether the difference between the first measurement vector and the second measurement vector exceeds or falls below a second upper and/or lower threshold value.

8. The method of claim 7, wherein a warning system with at least two warning levels is used to display the deviation of the actual state from the reference state and the difference between the first measurement vector and the second measurement vector, and wherein the warning system is based on a combination of the categories of the first type and the categories of the second type.

9. The method of claim 8, wherein the warning system displays, at time ti, the contribution of each measurement variable to the warning level and/or wherein the warning system displays, at time ti, the contribution of the categories of the first type and of the categories of the second type to the warning level.

10. The method of claim 1, wherein the step a is performed for at least two different reference states of the fluid, and wherein before the steps c-f are performed, the following method step is performed:
  selecting one of the at least two different reference states, wherein subsequently steps c-f are each preformed with respect to the respectively selected reference state.

11. The method of claim 10, wherein the at least two different reference states are defined by whether the fluid is subject to a pumping operation, and/or wherein the at least two different reference states are defined by whether the fluid originates in different springs, seawater plants and/or aquifers, wherein the fluid is untreated water and/or drinking water.

12. The method of claim 1, wherein the fluid is untreated water and/or drinking water.

13. The method of claim 1, wherein the measurement quantities are selected from the group consisting of fill level, temperature, turbidity, oxygen content, electrical conductivity, pressure, redox potential, flow rate, pH value, and spectral absorption coefficient.

14. A warning system for the automated in-line detection of deviations of an actual state of a fluid from a reference state of the fluid, with a measurement arrangement comprising:

at least three in-line measuring devices each configured to determine measured values, wherein the measured values captured substantially at the same time are evaluated in a combined manner with respect to at least three measurement variables, wherein the measurement variables are different measurement quantities of the fluid and/or a measurement quantity of the fluid measured at different measuring locations; and a computer program product, wherein the at least three in-line measuring devices and the computer program product are configured to execute a method comprising:

a. creating a reference data set by:
recurrently detecting reference measured values in-line at n different times, the reference measured values detected substantially simultaneously with respect to the at least three measurement variables, wherein the fluid is in the reference state when the reference measured values are detected;
storing the reference measured values;
arranging the reference measured values using a neural network and projection into a vector space having a reduced dimension, wherein the reduced dimension is smaller than the number of measurement variables such that the reference measured values detected at a given time are each mapped to a reference vector of the vector space; and
storing the n reference vectors;

b. performing an in-line measurement including:
in-line detection of substantially simultaneously detected measured values with respect to the at least three measurement variables of the fluid at a time ti; and
storing the measured values;

c. recurrently performing step b, wherein the measured values at time ti and the measured values at all times preceding time ti are recurrently arranged using the neural network and projected into the vector space of reduced dimension such that the measured values detected at time ti are mapped to a first measurement vector of the vector space;

d. storing the first measurement vector;

e. comparing the first measurement vector with the n reference vectors using a kernel density estimator of a window width using:

$$p_h(xti) = \frac{1}{nh^d} \sum_{j=1}^{n} f\left(\frac{|xti - rtj|}{h}\right)$$

wherein $p_h(xti)$ is the kernel density estimator, h is the window width, d is the vector space dimension, n is the number of reference vectors, xti is the first measurement vector, rtj is the reference vectors, and $$f\left(\frac{|xti - rtj|}{h}\right)$$

is a probability density function; and f. creating an assessment for the time ti with respect to a deviation of the actual state of the fluid from the reference state based on a value of the kernel density estimator.

15. The warning system of claim 14, wherein the computer program product is configured to perform the storing and/or processing of the reference measured values and/or the measured values at least partially on at least one server and/or in a cloud.

* * * * *